(12) United States Patent
Mutoh et al.

(10) Patent No.: US 11,464,762 B2
(45) Date of Patent: Oct. 11, 2022

(54) CARCINOGENESIS INHIBITOR

(71) Applicants: NATIONAL CANCER CENTER, Tokyo (JP); NIPPON ZOKI PHARMACEUTICAL CO., LTD., Osaka (JP)

(72) Inventors: Michihiro Mutoh, Tokyo (JP); Yurie Kurokawa, Tokyo (JP); Gen Fujii, Tokyo (JP); Shingo Miyamoto, Tokyo (JP)

(73) Assignees: NATIONAL CANCER CENTER, Tokyo (JP); NIPPON ZOKI PHARMACEUTICAL CO., LTD., Osaka (JP)

( * ) Notice: Subject to any disclaimer, the term of this patent is extended or adjusted under 35 U.S.C. 154(b) by 225 days.

(21) Appl. No.: 16/622,417

(22) PCT Filed: Jun. 12, 2018

(86) PCT No.: PCT/JP2018/022333
§ 371 (c)(1),
(2) Date: Dec. 13, 2019

(87) PCT Pub. No.: WO2018/230537
PCT Pub. Date: Dec. 20, 2018

(65) Prior Publication Data
US 2020/0276163 A1      Sep. 3, 2020

(30) Foreign Application Priority Data
Jun. 13, 2017  (JP) .............................. JP2017-115610

(51) Int. Cl.
A61K 31/4166     (2006.01)
A61P 35/00       (2006.01)
A61K 9/00        (2006.01)

(52) U.S. Cl.
CPC ........ A61K 31/4166 (2013.01); A61K 9/0056 (2013.01); A61P 35/00 (2018.01)

(58) Field of Classification Search
None
See application file for complete search history.

(56) References Cited

U.S. PATENT DOCUMENTS

| 5,084,473 | A | 1/1992 | Mikami et al. |
| 6,197,806 | B1 | 3/2001 | Endou et al. |
| 6,251,929 | B1 | 6/2001 | Naiki et al. |
| 8,609,075 | B2 | 12/2013 | Iriyama et al. |
| 8,901,160 | B2 | 12/2014 | Iriyama et al. |
| 2002/0147228 | A1 | 10/2002 | Ienaga et al. |
| 2009/0215730 | A1* | 8/2009 | Rodriguez Fernandez ................ C07C 327/42 514/645 |
| 2012/0183481 | A1 | 7/2012 | Iriyama et al. |
| 2014/0080878 | A1 | 3/2014 | Iriyama et al. |
| 2017/0065563 | A1 | 3/2017 | Ienaga |

FOREIGN PATENT DOCUMENTS

| JP | S57-114578 A | 7/1982 |
| JP | S60-188373 A | 9/1985 |
| JP | S61-122275 A | 6/1986 |
| JP | S62-000014 A | 1/1987 |
| JP | S62-045525 A | 2/1987 |
| JP | S62-145068 A | 6/1987 |
| JP | H01-075473 A | 3/1989 |
| JP | H01-299276 A | 12/1989 |
| JP | H03-072463 A | 3/1991 |
| JP | H09-227377 A | 9/1997 |
| JP | 2000-212083 A | 8/2000 |
| JP | 2002-121132 A | 4/2002 |
| JP | 2002-241283 A | 8/2002 |
| RU | 2503454 C1 | 1/2014 |
| WO | 2005/090316 A1 | 9/2005 |
| WO | 2015/129750 A1 | 9/2015 |

OTHER PUBLICATIONS

Aiello. Marine Drugs, 2011, 9, 1157-1165. (Year: 2011).*
Oct. 14, 2021 Office Action issued in Rusian Patent Application No. 2020100037.
Mohammad A. Khanfar et al., "Phenylmethylene hydantoins as prostate cancer invasion and migration inhibitors. CoMFA approach and QSAR analysis" European Journal of Medicinal Chemistry, vol. 45, No. 11, pp. 5397-5405, 2010.
Yurie Kurokawa et al., "The Radical Scavenger NZ-419 Suppresses Intestinal Polyp Development in Ape-Mutant Mice" Journal of Clinical Medicine, vol. 9, No. 1, p. 270, 2020.
Feb. 17, 2021 Extended European Search Report issued in European Patent Application No. 18816986.6.
Sep. 11, 2018 Written Opinion of the International Searching Authority issued in International Patent Application No. PCT/JP2018/022333.
Satoshi Kokura et al. "Carcinogenesis due to Free Radicals and Carcinogenesis Preventive Effects of Ginkgo Leave Extracts". vol. 38, Journal of Clinical Biochemistry and Nutrition, pp. 69-71, 2006.
Y. Levo et al. "Hydantoin Immunosuppression and Carcinogenesis" Clinical & Experimental Immunology, vol. 19, No. 3, pp. 521-527, 1975.
Sep. 11, 2018 International Search Report issued International Patent Application No. PCT/JP2018/022333.

* cited by examiner

*Primary Examiner* — Noble E Jarrell
(74) *Attorney, Agent, or Firm* — Oliff PLC

(57) ABSTRACT

A carcinogenesis inhibitor having no side effect and having an excellent effect by oral administration. A carcinogenesis inhibitor containing a hydantoin derivative or a pharmaceutically acceptable salt thereof as an active ingredient shows an inhibiting action for polyp formation and for cell proliferation, and has no side effect and highly safe whereby it is very highly useful as a pharmaceutical agent and a food such as supplement which prevent the occurrence and progress of cancer, inhibits the recurrence and metastasis of cancer and further achieves the therapeutic effect.

10 Claims, 1 Drawing Sheet
Specification includes a Sequence Listing.

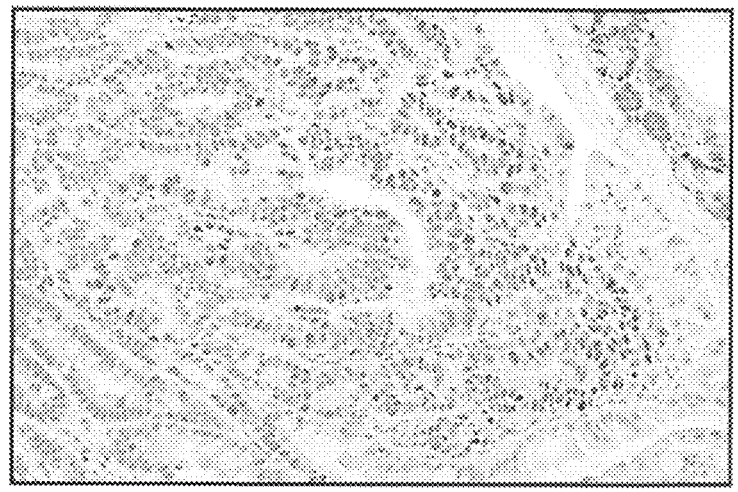
Control group
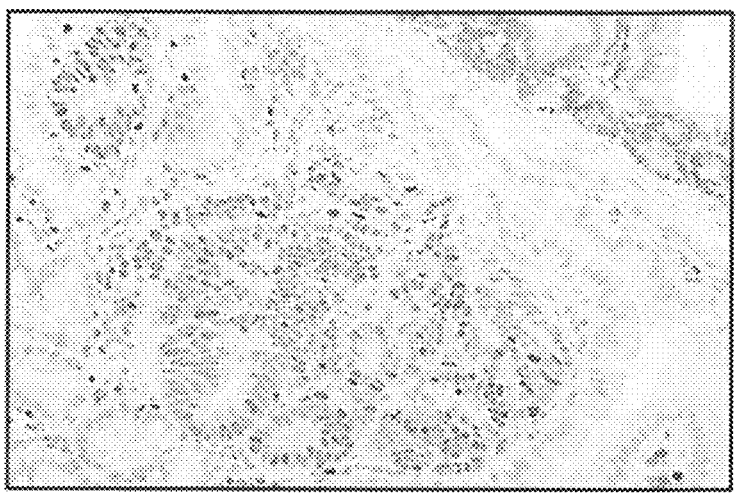
1000ppm test substance-administering group

CARCINOGENESIS INHIBITOR

TECHNICAL FIELD

The present invention relates to a novel pharmaceutical use of a hydantoin derivative or a pharmaceutically acceptable salt thereof. More particularly, it relates to a carcinogenesis inhibitor containing at least one member of a hydantoin derivative or a pharmaceutically acceptable salt thereof as an active ingredient.

BACKGROUND ART

Due to the factors such as the worldwide aging of society, the westernization of dietary habits, the smoking habit, etc., it has been presumed that numbers of the patients suffering from cancer will be increasing in future not only in Japan but also in the world. According to "Reports on Cancer in the World (2014)" edited by the Word Health Organization (WHO), numbers of patients suffering from cancer in the world has been increasing year by year starting from 14 millions in 2012 and are estimated to be 19 millions in 2025 and 24 millions in 2035. On the other hand, although various therapeutic methods such as surgical therapy, radiation therapy, chemotherapy, thermotherapy, immunotherapy, photodynamic therapy, etc. have been used, there has been no therapeutic method which is able to completely cure any cancer. Even if the cancer therapy seems to be well done, there may happen such an outcome that the cancer cells which are not well excised in the case of surgical therapy or the once-reduced cancer cells in the case of chemotherapy or radiation therapy are proliferated again in the same or adjacent area (Hereinafter, it will be referred to as "recurrence".). There may also happen such an outcome that the same cancer appears in other area than the original one (Hereinafter, it will be referred to as "metastasis".). In view of the above, it is impossible even at present to completely cure all types of cancer. Therefore, it has been strongly expected in medical site that the effective means preventing the recurrence and the metastasis which make the therapy of cancer particularly difficult are provided.

In view of the above, the viewpoint of carcinogenesis inhibition where occurrence of the cancer is prevented or possibility of occurrence of the cancer is reduced has been emphasized in recent years separately from the therapy after occurrence of cancer. The most well-known means for carcinogenesis inhibition is a re-examination in the lifestyle habit such as nonsmoking and improvement of meals. For example, in the causes of death by cancer of American people reported by Harvard Center for Cancer Prevention in 1996, smoking is mentioned to be 30% and a diet is also as high as 30%. On the other hand, usefulness of chemoprevention where vitamin preparations, pharmaceutical agents, etc. are positively administered has been investigated. Subjects for the chemoprevention include high-risk groups having the high possibility of becoming cancer such as smokers, persons having the high possibility of becoming cancer genetically or professionally, persons having precancerous lesion such as a colorectal polyp and persons who once finished the cancer therapy. The requirement to adopt the chemoprevention as such is that the risk of side effect is low, although it is a matter of course that the efficacy is certified. In addition, if the chemoprevention is able to be done by a medicine or a food (such as supplement or healthy food) which can be orally taken with ease in daily life, that is very simple, convenient and preferred. When excellent chemoprevention for cancer is realized, it is undoubtedly the excellently good news for persons worrying about the occurrence of cancer and also being terrified by the recurrence or the metastasis of cancer. Further, diffusion of the cancer chemoprevention will greatly improve the treatment outcome (the survival advantage) and, at the same time, it will contribute in the avoidance of repeated surgical operations, in the reduction of medical expenses caused by the fact that prescription of expensive anti-cancer agent, etc. becomes unnecessary and in the inhibition of social loss by the fact that the patients suffering from cancer are able to be continuously work.

In the development of pharmaceuticals for the cancer chemoprevention as such, the way of thinking called drug repositioning has been receiving the public attention. The drug repositioning is a research means of finding the new pharmaceutical effects other than the conventionally known ones from the existing drugs or the developing drugs where safety, internal kinetics, etc. have been established or confirmed already and of resulting in practical use. Both of the "reliability" due to the fact that it has a track record of use for humans by being put into the market and the safety and the internal kinetics have been already confirmed in a clinical level and the "low cost" due to the fact that many prior existing data are able to be used are the highest advantages in view of the development of pharmaceuticals.

As a result of the researches of cancer being carried out throughout the world up to now, many things have been also clarified already in the factors concerning the initial stage of cancer occurrence and in the important signaling pathway route in which such factors are participated. As to the precancerous symptoms highly related to the signal pathway, there are exemplified "inflammation", "oxidative stress" and "maintenance of undifferentiated state" and they have been said to be characterized by a transcription control via a specific transcription factor. Accordingly, there will be a possibility that the regulation of the transcription control as such results in the carcinogenesis inhibition and it has been expected that anti-inflammatory agents and antioxidants are able to be the candidates of carcinogenesis inhibitors. Actually, in the International Agency for Research on Cancer (IARC), the anti-inflammatory agents such as sulindac and indomethacin and the antioxidants such as β-carotene and retinoic acid have been evaluated whether they exhibit the cancer-preventive effect. Unfortunately however, among the substances evaluated as such, there is almost no one, at present, being equipped with the sufficient scientific evidence for exhibiting the cancer-preventing effect.

A hydantoin derivative or a pharmaceutically-acceptable salt thereof which is the active ingredient of the carcinogenesis inhibitor according to the present invention (Hereinafter, it will be referred to as "the present compound". Moreover, even when such a case where a simple expression reading "a compound" is used, it may sometimes cover a pharmaceutically acceptable salt thereof.) has been found as a novel substance having a controlling action for plant growth by Nippon Zoki Pharmaceutical Co., Ltd. which is an applicant for the present application. As a result of the studies thereafter, the present compound has been reported to have pharmacological actions such as hypoglycemic action and hypolipidemic action and to be lowly toxic and to have almost no side effect (cf. Japanese Patent Laid-Open No. 57/114578 A, 60/188373 A, 61/122275 A, 62/45525 A, 62/000014 A, 01/75473 A, 01/299276 A, etc.). In addition, as to other pharmaceutical uses of the present compound, there have been filed patent applications as an agent for lowering the toxin for uremia (Japanese Patent Laid-Open No. 03/072463 A), a therapeutic agent for intractable vasculitis (Japanese Patent Laid-Open No. 2000/212083 A), an improving agent for hypoalbuminemia (Japanese Patent Laid-Open No. 2002/241283 A) and a progress-suppressing or improving agent for chronic kidney disease (International Publication No. WO 2015/129750 A1) and the effects have been disclosed therein.

In the meanwhile, during its clinical tests for the development as the therapeutic agent for chronic kidney disease, the present compound has been confirmed to have high safety in humans.

Incidentally, Patent Document 1 discloses that the present compound is useful as an eliminating agent for activated oxygen and free radicals. As mentioned above, the possibility that an antioxidant substance will be able to be effective for the inhibition of carcinogenesis has been known already. Actually however, as things are, all antioxidant substances do not always exhibit the carcinogenesis inhibiting effect but only a part of antioxidant substances have been confirmed to exhibit the carcinogenesis inhibiting effect. In addition, even in the antioxidant substances exhibiting the carcinogenesis inhibiting action, it has been also found that the carcinogenesis inhibiting action is achieved due to an anti-inflammatory action or an enzyme-inhibiting action instead of due to the antioxidant action. It is likely that the antioxidant substance as such inhibits the progress of precancerous symptom to cancer by participating in "inflammation" and "maintenance of undifferentiated state" instead of in "oxidative stress" among the above-mentioned precancerous symptoms of "inflammation", "oxidative stress" and "maintenance of undifferentiated state".

In Patent Document 1, there is neither description nor suggestion at all for the fact that the present compound exhibits a carcinogenesis inhibiting effect. As mentioned above, it has been known already that even the substances which have been known as the so-called antioxidant do not always achieve the carcinogenesis inhibiting effect. In addition, although various substances such as anti-inflammation agent and enzyme-inhibiting agent other than the antioxidant are able to be candidate substances for the carcinogenesis inhibitors, it is very rare that such substances actually exhibit a carcinogenesis inhibiting action and moreover that they are the substances being able to be orally administered or ingested and having low risk of side effects. As will be mentioned later, the present compound can be an excellent carcinogenesis inhibitor satisfying several requirements as such.

PRIOR ART DOCUMENTS

Patent Documents

Patent Document 1: Japanese Patent Laid-Open No. 09/227377 A

SUMMARY OF THE INVENTION

Problem to be Solved by the Invention

An object of the present invention is to provide a carcinogenesis inhibitor having such an effect of preventing the carcinogenesis and of lowering the possibility (probability) of the carcinogenesis including primary occurrence, recurrence and metastasis of cancer (It is referred to as "carcinogenesis inhibition" in the present application.), having a low risk of side effects and being able to be orally administered or ingested. The carcinogenesis inhibitor of the present invention is made the inhibition of occurrence, recurrence and metastasis of cancer possible by administration or ingestion particularly to persons having a high risk of carcinogenesis or to patients during and after the treatment of cancer. As to the dosage form thereof, the most preferred ones are the pharmaceutical agent being able to be ingested (orally administered) and the food such as supplement being able to be orally ingested.

Means for Solving the Problems

The present inventors have repeatedly conducted studies for chemopreventing agents for cancer. Now, a pharmacological test by oral administration to Min mice model of a familial adenomatosis coli was conducted using a hydantoin derivative represented by the following formula (I) or a pharmaceutically acceptable salt thereof (the present compound). It was confirmed that the present compound inhibited the expression of the cell proliferation-associated factors which were c-Myc, CDK4 and cyclin D1 in an intestinal epithelial mucous tissue and a polyp part thereof and the cell proliferation ability in the polyp part. It was also confirmed that the expression of the antioxidation-associated factor Gpx2 in an intestinal epithelial mucous tissue of the Min mice was promoted. On the other hand, it was noted that the present compound resulted in a change in the transcriptional regulation system of the Keap1-Nrf2 pathway by eliminating the reactive oxygen species (ROS) produced in the human colon cancer cell HCT-116 during the treatment of hydrogen peroxide (11202) which is a radical generator. In view of those facts, the present inventors experimentally confirmed that the present compound had an excellent carcinogenesis inhibiting action.

On the other hand, in the studies in the past, the present compound was confirmed to be safe not only in animals such as rats and dogs but also in humans whereby it also meets the requirement that the risk of side effects is low which is to be considered to be important as a chemoprevention agent for cancer. Moreover, in the drugs which have been recognized to be safe as a ROS eliminating agent, there was only an agent for intravenous injection as a dosage form while the present compound showed an effective action by oral administration whereby it is significantly highly advantageous in terms of administration and ingestion. Such being the case, the carcinogenesis inhibitor of the present invention has a possibility of being able to be used not only as a pharmaceutical agent but also as a food (health food, supplement, etc.). In the meanwhile, the carcinogenesis inhibitor of the present invention is able to be used not only for humans but also for animals (particularly for mammals) whereby the carcinogenesis inhibitor of the present invention is not limited to be used only for humans. In view of the above, the present inventors have now found that the present compound is able to be used as an excellent carcinogenesis inhibitor and accomplished the present invention. Thus, the present invention is related to the following items although it is never limited thereto.

(1) A carcinogenesis inhibitor containing at least one member of a hydantoin derivative represented by the following formula (I) and a pharmaceutically acceptable salt thereof as an active ingredient:

[chem. 1]

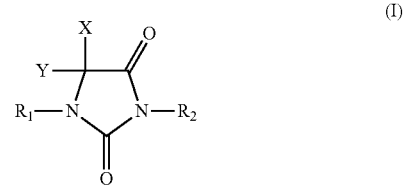

wherein $R_1$ and $R_2$ are same or different and each is hydrogen, alkyl, cycloalkyl or benzyl which may be substituted with one or two halogen(s), nitro(s), alkyl(s) or alkoxy(s) and X and Y are same or different and each is hydrogen, carboxy, alkyl or alkoxy.

(2) The carcinogenesis inhibitor according to the above (1), wherein $R_1$ and $R_2$ are same or different and each is hydrogen or alkyl having 1 to 3 carbon(s) and X and Y are same or different and each is hydrogen, carboxy or alkoxy having 1 to 3 carbon(s).

(3) The carcinogenesis inhibitor according to the above (1) or (2), wherein $R_1$ is alkyl having 1 to 3 carbon(s) and $R_2$ is hydrogen.

(4) The carcinogenesis inhibitor according to any of the above (1) to (3), wherein $R_1$ is alkyl having 1 to 2 carbon(s) and $R_2$ is hydrogen.

(5) The carcinogenesis inhibitor according to any of the above (1) to (4), wherein $R_1$ is methyl and $R_2$ is hydrogen.

(6) The carcinogenesis inhibitor according to any of the above (1) to (5), wherein one of X and Y is hydrogen and the other is carboxy.

(7) The carcinogenesis inhibitor according to any of the above (1) to (6), wherein the carcinogenesis inhibition is caused by an inhibition of polyp formation.

(8) The carcinogenesis inhibitor according to any of the above (1) to (7), wherein the carcinogenesis inhibition is caused by a regulation of expression of an antioxidation-associated factor.

(9) The carcinogenesis inhibitor according to the above (8), wherein the carcinogenesis inhibition is caused by a promotion of expression of Gpx2.

(10) The carcinogenesis inhibitor according to any of the above (1) to (9), wherein the carcinogenesis inhibition is caused by an elimination of ROS.

(11) The carcinogenesis inhibitor according to any of the above (1) to (10), wherein the carcinogenesis inhibition is caused by a regulation of expression of cell proliferation-associated factors.

(12) The carcinogenesis inhibitor according to the above (11), wherein the carcinogenesis inhibition is caused by an inhibition of expression of c-Myc, CDK4 or cyclin D1.

(13) The carcinogenesis inhibitor according to any of the above (1) to (12), wherein it is a carcinogenesis inhibitor for digestive tract cancer.

(14) The carcinogenesis inhibitor according to the above (13), wherein it is a carcinogenesis inhibitor for colon cancer.

(15) The carcinogenesis inhibitor according to any of the above (1) to (14), wherein it is a pharmaceutical composition.

(16) The carcinogenesis inhibitor according to the above (15), wherein it is an oral preparation.

(17) The carcinogenesis inhibitor according to the above (15), wherein it is an injection preparation.

(18) The carcinogenesis inhibitor according to any of the above (1) to (14), wherein it is a food composition.

(19) The carcinogenesis inhibitor according to the above (18), wherein it is a health food or a supplement.

(20) A method for inhibiting a carcinogenesis, comprising administrating an effective amount of at least one member of the hydantoin derivative and the pharmaceutically acceptable salt thereof mentioned in any of the above (1) to (6) to a subject in need thereof.

(21) The method for inhibiting the carcinogenesis according to the above (20), wherein the carcinogenesis inhibition is done by inhibition of polyp formation.

(22) The method for inhibiting the carcinogenesis according to the above (20) or (21), wherein the carcinogenesis inhibition is done by regulation of expression of an antioxidation-associated factor.

(23) The method for inhibiting the carcinogenesis according to the above (22), wherein the carcinogenesis inhibition is done by promotion of expression of Gpx2.

(24) The method for inhibiting the carcinogenesis according to any of the above (20) to (23), wherein the carcinogenesis inhibition is done by elimination of ROS.

(25) The method for inhibiting the carcinogenesis according to any of the above (20) to (24), wherein the carcinogenesis inhibition is done by regulation of expression of a cell proliferation-associated factor.

(26) The method for inhibiting the carcinogenesis according to the above (25), wherein the carcinogenesis inhibition is done by inhibition of expression of c-Myc, CDK4 or cyclin D1.

(27) The method for inhibiting the carcinogenesis according to any of the above (20) to (26), wherein the occurrence of digestive tract cancer is inhibited.

(28) The method for inhibiting the carcinogenesis according to the above (27), wherein the occurrence of colon cancer is inhibited.

(29) The method for inhibiting the carcinogenesis according to any of the above (20) to (28), comprising administrating a pharmaceutical composition containing at least one member of the hydantoin derivative and the pharmaceutically acceptable salt thereof.

(30) The method for inhibiting the carcinogenesis according to the above (29), wherein the pharmaceutical composition is an oral preparation.

(31) The method for inhibiting the carcinogenesis according to the above (29), wherein the pharmaceutical composition is an injection preparation.

(32) The method for inhibiting the carcinogenesis according to any of the above (20) to (28), comprising administrating a food composition containing at least one member of the hydantoin derivative and the pharmaceutically acceptable salt thereof.

(33) The method for inhibiting the carcinogenesis according to the above (32), wherein the food composition is health food or supplement.

(34) The hydantoin derivative or the pharmaceutically acceptable salt thereof mentioned in any of the above (1) to (6) for use in inhibiting a carcinogenesis.

(35) The hydantoin derivative or the pharmaceutically acceptable salt thereof for use according to the above (34), wherein the carcinogenesis inhibition is done by inhibition of polyp formation.

(36) The hydantoin derivative or the pharmaceutically acceptable salt thereof for use according to the above (34) or (35), wherein the carcinogenesis inhibition is done by regulation of expression of an antioxidation-associated factor.

(37) The hydantoin derivative or the pharmaceutically acceptable salt thereof for use according to the above (36), wherein the carcinogenesis inhibition is done by promotion of expression of Gpx2.

(38) The hydantoin derivative or the pharmaceutically acceptable salt thereof for use according to any of the above (34) to (37), wherein the carcinogenesis inhibition is done by elimination of ROS.

(39) The hydantoin derivative or the pharmaceutically acceptable salt thereof for use according to any of the above (34) to (38), wherein the carcinogenesis inhibition is done by regulation of expression of a cell proliferation-associated factor.

(40) The hydantoin derivative or the pharmaceutically acceptable salt thereof for use according to the above (39), wherein the carcinogenesis inhibition is done by inhibition of expression of c-Myc, CDK4 or cyclin D1.

(41) The hydantoin derivative or the pharmaceutically acceptable salt thereof for use according to any of the above (34) to (40), wherein it inhibits the occurrence of digestive cancer.

(42) The hydantoin derivative or the pharmaceutically acceptable salt thereof for use according to the above (41), wherein it inhibits the occurrence of colon cancer.

(43) The hydantoin derivative or the pharmaceutically acceptable salt thereof for use according to any of the above (34) to (42), wherein it is a pharmaceutical composition.

(44) The hydantoin derivative or the pharmaceutically acceptable salt thereof for use according to the above (43), wherein the pharmaceutical preparation is an oral preparation.

(45) The hydantoin derivative or the pharmaceutically acceptable salt thereof for use according to the above (43), wherein the pharmaceutical preparation is an injection preparation.

(46) The hydantoin derivative or the pharmaceutically acceptable salt thereof for use according to any of the above (34) to (42), wherein it is a food composition.

(47) The hydantoin derivative or the pharmaceutically acceptable salt thereof for use according to the above (46), wherein the food composition is health food or supplement.

(48) Use of the hydantoin derivative or the pharmaceutically acceptable salt thereof mentioned in any of the above (1) to (6) in the manufacture of a carcinogenesis inhibitor.

(49) The use of the hydantoin derivative or the pharmaceutically acceptable salt thereof according to the above (48), wherein the carcinogenesis inhibition is done by inhibition of polyp formation.

(50) The use of the hydantoin derivative or the pharmaceutically acceptable salt thereof according to the above (48) or (49), wherein the carcinogenesis inhibition is done by regulation of expression of an antioxidation-associated factor.

(51) The use of the hydantoin derivative or the pharmaceutically acceptable salt thereof according to the above (50), wherein the carcinogenesis inhibition is done by promotion of expression of Gpx2.

(52) The use of the hydantoin derivative or the pharmaceutically acceptable salt thereof according to any of the above (48) to (51), wherein the carcinogenesis inhibition is done by elimination of ROS.

(53) The use of the hydantoin derivative or the pharmaceutically acceptable salt thereof according to any of the above (48) to (52), wherein the carcinogenesis inhibition is done by regulation of expression of a cell proliferation-associated factor.

(54) The use of the hydantoin derivative or the pharmaceutically acceptable salt thereof according to the above (53), wherein the carcinogenesis inhibition is done by inhibition of expression of c-Myc, CDK4 or cyclin D1.

(55) The use of the hydantoin derivative or the pharmaceutically acceptable salt thereof according to any of the above (48) to (54), wherein it is a carcinogenesis inhibitor for digestive cancer.

(56) The use of the hydantoin derivative or the pharmaceutically acceptable salt thereof according to the above (55), wherein it is a carcinogenesis inhibitor for colon cancer.

(57) The use of the hydantoin derivative or the pharmaceutically acceptable salt thereof according to any of the above (48) to (56), wherein the carcinogenesis inhibitor is a pharmaceutical composition.

(58) The use of the hydantoin derivative or the pharmaceutically acceptable salt thereof according to the above (57), wherein the pharmaceutical composition is an oral preparation.

(59) The use of the hydantoin derivative or the pharmaceutically acceptable salt thereof according to the above (57), wherein the pharmaceutical composition is an injection preparation.

(60) The use of the hydantoin derivative or the pharmaceutically acceptable salt thereof according to any of the above (48) to (56), wherein the carcinogenesis inhibitor is a food composition.

(61) The use of the hydantoin derivative or the pharmaceutically acceptable salt thereof according to the above (60), wherein the food composition is health food or supplement.

Advantages of the Invention

In the pharmacological test which will be mentioned later, the present compound showed an excellent inhibitive effect against the formation of polyp and the expression of a cell proliferation-associated factor. In addition, since the present compound shows very high safety and achieves an effect by oral administration and ingestion, it is able to become a very highly useful carcinogenesis inhibitor whereby chemoprevention is able to be made possible in the dosage form such as pharmaceutical agent or food.

BRIEF DESCRIPTION OF DRAWINGS

FIG. 1 is an optical microscope photograph showing the result of a PCNA immunostaining in a polyp part of a mouse small intestinal mucosa of a control group and of a group administered with 1000 ppm of a tested substance.

MODE FOR CARRYING OUT THE INVENTION

The present invention relates to a carcinogenesis inhibitor containing at least one member of a hydantoin derivative represented by the following formula (I) and a pharmaceutically acceptable salt thereof as an active ingredient.

[chem. 2]

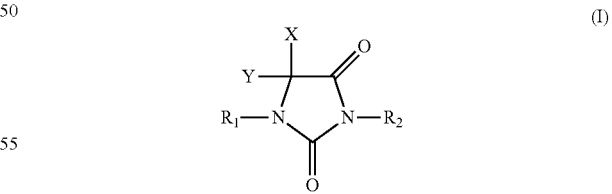

wherein $R_1$ and $R_2$ are same or different, and each is hydrogen, alkyl, cycloalkyl or benzyl which may be substituted with one or two halogen(s), nitro(s), alkyl(s) or alkoxy(s) and X and Y are same or different and each is hydrogen, carboxy, alkyl or alkoxy.

In the substituents in the above formula (I), although the alkyl may be any alkyl, it is preferably a linear or branched alkyl group having 1 to 20 carbon(s) such as methyl, ethyl, propyl, isopropyl, butyl, isobutyl, sec-butyl, t-butyl, pentyl, isopentyl, neopentyl, t-pentyl, hexyl, isohexyl, heptyl, isoheptyl, octyl, isooctyl, nonyl, isononyl, decyl, isodecyl or stearyl, more preferably, a linear or branched alkyl having 1 to 6 carbon(s), still more preferably, a linear or branched alkyl group having 1 to 3 carbon(s).

In the substituents in the above formula (I), although the cycloalkyl may be any cycloalkyl, it is preferably a cycloalkyl group having 3 to 8 carbons such as cyclopropyl, cyclobutyl, cyclopentyl, cyclohexyl, cycloheptyl and cyclooctyl and, more preferably, it is a cycloalkyl group having 5 to 6 carbons.

In the substituents in the above formula (I), although the alkoxy may be any alkoxy, it is preferably a linear or branched alkoxy group having 1 to 6 carbon(s) such as methoxy, ethoxy, propoxy, isopropoxy, butoxy, isobutoxy, sec-butoxy, t-butoxy, pentoxy and hexoxy and, more preferably, a linear or branched alkoxy group having 1 to 3 carbon(s).

In the substituents in the above formula (I), although the halogen may be any halogen, it is preferably fluorine, chlorine, bromine, iodine or the like.

The general production method and production examples of the present compound are disclosed in Japanese Patent Laid-Open No. 61/122275 A, Japanese Patent Laid-Open No. 62/145068 A, etc. Hereinafter, examples of the present compound are shown. When each of the compounds is referred to hereinafter, the compound number will be used.

Hydantoin [Compound 1]
1-Methylhydantoin [Compound 2]
3-Methylhydantoin [Compound 3]
1-Ethylhydantoin [Compound 4]
1-Propylhydantoin [Compound 5]
1-Butylhydantoin [Compound 6]
1-t-Butylhydantoin [Compound 7]
1-Hexylhydantoin [Compound 8]
1-(1,3-Dimethylbutyl)hydantoin [Compound 9]
1-Decylhydantoin [Compound 10]
1-Stearylhydantoin [Compound 11]
1,3-Dimethylhydantoin [Compound 12]
1,5-Dimethylhydantoin [Compound 13]
3,5-Dimethylhydantoin [Compound 14]
1-Cyclopentylhydantoin [Compound 15]
1-Cyclohexylhydantoin [Compound 16]
1-Cyclohexyl-3-methylhydantoin [Compound 17]
3-Cyclohexylhydantoin [Compound 18]
1,3-Dicyclohexylhydantoin [Compound 19]
5-Hydroxyhydantoin [Compound 20]
5-Hydroxy-1-methylhydantoin [Compound 21]
5-Hydroxy-3-methylhydantoin [Compound 22]
5-Hydroxy-1-ethylhydantoin [Compound 23]
5-Hydroxy-1-propylhydantoin [Compound 24]
5-Hydroxy-1-butylhydantoin [Compound 25]
5-Hydroxy-1-t-butylhydantoin [Compound 26]
5-Hydroxy-1-hexylhydantoin [Compound 27]
5-Hydroxy-1-(1,3-dimethylbutyl)hydantoin [Compound 28]
5-Hydroxy-1-decylhydantoin [Compound 29]
5-Hydroxy-1-stearylhydantoin [Compound 30]
5-Hydroxy-1-cyclopentylhydantoin [Compound 31]
5-Hydroxy-1-cyclohexylhydantoin [Compound 32]
5-Hydroxy-1-cyclohexyl-3-methylhydantoin [Compound 33]
5-Hydroxy-1,3-dimethylhydantoin [Compound 34]
5-Hydroxy-1,5-dimethylhydantoin [Compound 35]
5-Hydroxy-3,5-dimethylhydantoin [Compound 36]
5-Hydroxy-1,3-dicyclohexylhydantoin [Compound 37]
5-Methoxyhydantoin [Compound 38]
5-Methoxy-1-methylhydantoin [Compound 39]
5-Methoxy-3-methylhydantoin [Compound 40]
5-Methoxy-1-ethylhydantoin [Compound 41]
5-Methoxy-1-propylhydantoin [Compound 42]
5-Methoxy-1-butylhydantoin [Compound 43]
5-Methoxy-1-cyclohexylhydantoin [Compound 44]
5-Methoxy-3-cyclohexylhydantoin [Compound 45]
5-Ethoxyhydantoin [Compound 46]
5-Ethoxy-1-methylhydantoin [Compound 47]
5-Ethoxy-3-methylhydantoin [Compound 48]
5-Ethoxy-1-ethylhydantoin [Compound 49]
5-Ethoxyl-1-propylhydantoin [Compound 50]
5-Ethoxy-1-butylhydantoin [Compound 51]
5-Propoxyhydantoin [Compound 52]
5-Propoxy-1-methylhydantoin [Compound 53]
5-Propoxy-3-methylhydantoin [Compound 54]
5-Propoxy-1-ethylhydantoin [Compound 55]
5-Propoxy-1-propylhydantoin [Compound 56]
5-Propoxy-1-butylhydantoin [Compound 57]
5-Butoxyhydantoin [Compound 58]
5-Butoxy-1-methylhydantoin [Compound 59]
5-Butoxy-3-methylhydantoin [Compound 60]
5-t-Butoxyhydantoin [Compound 61]
5-t-Butoxy-1-methylhydantoin [Compound 62]
5-t-Butoxy-3-butylhydantoin [Compound 63]
5-Hydroxy-1-benzylhydantoin [Compound 64]
5-Hydroxy-1-(2-fluorobenzyl)hydantoin [Compound 65]
5-Hydroxy-1-(3-fluorobenzyl)hydantoin [Compound 66]
5-Hydroxy-1-(4-fluorobenzyl)hydantoin [Compound 67]
5-Hydroxy-1-(2-chlorobenzyl)hydantoin [Compound 68]
5-Hydroxy-1-(4-chlorobenzyl)hydantoin [Compound 69]
5-Hydroxy-1-(4-bromobenzyl)hydantoin [Compound 70]
5-Hydroxy-1-(3-nitrobenzyl)hydantoin [Compound 71]
5-Hydroxy-1-(4-nitrobenzyl)hydantoin [Compound 72]
5-Hydroxy-1-(2-methylbenzyl)hydantoin [Compound 73]
5-Hydroxy-1-(3-methylbenzyl)hydantoin [Compound 74]
5-Hydroxy-1-(4-methylbenzyl)hydantoin [Compound 75]
5-Hydroxy-1-(2-methoxybenzyl)hydantoin [Compound 76]
5-Hydroxy-1-(3-methoxybenzyl)hydantoin [Compound 77]
5-Hydroxy-1-(4-methoxybenzyl)hydantoin [Compound 78]
5-Hydroxy-1-(3,4-dimethoxybenzyl)hydantoin [Compound 79]
5-Hydroxy-1-(3,4-dichlorobenzyl)hydantoin [Compound 80]

The present compound includes a salt of a compound represented by the above formula (I) and examples thereof include an addition salt with an acid such as hydrochloric acid, sulfuric acid, nitric acid, hydrobromic acid, phosphoric acid, perchloric acid, thiocyanic acid, boric acid, formic acid, acetic acid, haloacetic acid, propionic acid, glycolic acid, citric acid, tartaric acid, succinic acid, gluconic acid, lactic acid, malonic acid, fumaric acid, anthranilic acid, benzoic acid, cinnamic acid, p-toluenesulfonic acid, naphthalenesulfonic acid or sulfanilic acid; and a salt with alkali metal such as sodium or potassium, with alkali earth metal such as calcium, magnesium or barium and with metal such as aluminum or zinc. The salts as such may be produced from a free hydantoin derivative by a known method or may be converted each other.

Even when the present compound is present in a form of a stereoisomer such as cis-trans isomer, optical isomer or conformational isomer, or in a state of hydrate or complex, the present invention covers any of such stereoisomers, hydrates and complex compounds thereof. For example, in the present compound 5-hydroxy-1-methylhydantoin, 5-position of the hydantoin ring is an asymmetric carbon whereby optical isomers, S enantiomer and R enantiomer, are present. The present invention covers the S and R enantiomers as such and a mixture thereof. In addition, it has been known that, in the present compound 5-hydroxy-1-methylhydantoin, there are crystal polymorphisms of form I and form II thereof and the present compound covers various crystal forms (polymorphisms) being able to be formed including the above crystals.

The present compound may be made into a pharmaceutical agent by appropriately combining with an appropriate carrier or diluent for pharmaceutical use. In addition to oral preparations such as tablets, capsules, powders and liquid, it is also possible, if desired, to make into parenteral preparations such as those for hypodermic, intravenous, intramuscular, intrarectal and intranasal administrations. However, as mentioned above, the dosage form is preferred to be an oral preparation in the case of administration/ingestion as the carcinogenesis inhibitor of the present invention.

In the prescriptions, the present compound may be used in a pharmaceutically acceptable salt thereof or may be used either solely or jointly in an appropriate combination. It also may be made into a combination drug with other pharmaceutically active ingredient.

As to the oral preparation, it is possible to make into tablets, diluted powder, granules or capsules either as it is or by appropriately combining with appropriate additives such as a commonly used excipient (e.g., lactose, mannitol, corn starch, potato starch or calcium citrate) together with a cellulose derivative (e.g., crystalline cellulose or hydroxypropyl cellulose), a binder (e.g., acacia, corn starch or gelatin), a disintegrator (e.g., corn starch, potato starch or carboxymethyl cellulose calcium), a lubricant (e.g., talc or magnesium stearate) and others (e.g., extender, moisturizer, buffer, preservative or fragrance) in an appropriate combination.

As to the injection preparation, it is possible to make into solution, suspension or emulsion of an aqueous solvent (such as distilled water for injection, physiological saline solution or injection solution of glucose) or of a non-aqueous solvent (such as vegetable oil, synthetic fatty acid glyceride, higher fatty acid ester or propylene glycol). If necessary, it is also possible to appropriately add a commonly used additive such as dissolving adjuvant, isotonicifier, suspending agent, emulsifying agent, stabilizer or preservative thereto.

Further, depending upon the disease type and the patient, it is also possible to make into other dosage forms being suitable for the treatment such as syrup, suppository, inhalation agent, aerosol preparation, eye drops and topical preparation (e.g., ointment, gel preparation or adhesive skin patch).

It is further possible that the present compound is used as a health food or a supplement either by using the present compound per se or by mixing with other ingredient. As to the other ingredient to be mixed, there is no particular limitation so far as it is not denatured by the mixing and the examples thereof include food and beverage. There is no particular limitation for the food and the beverage and examples thereof include chocolate, chewing gum, yogurt, refreshing beverage, coffee, tea, alcoholic beverage, biscuit, bread and jelly.

In the manufacture of the food and the beverage, various substances may be added upon necessity. Examples thereof include saccharide such as sucrose, fructose or glucose; sugar alcohol such as xylitol or erythritol; antioxidant such as amino acid, citric acid, lactic acid, malic acid, flavonoid or catechin. In addition thereto, any other substance which has been used in the usual manufacture of food such as gelatin, vitamins, dye, fragrance, calcium preparation, glycerol fatty acid ester or pectin may be appropriately used.

The carcinogenesis inhibitor of the present invention is useful not only for the prevention for persons where no cancer occurs yet but also for the prevention of recurrence after the cancer therapy and for the prevention of metastasis for persons during the cancer therapy. Examples of the subject for administration of the carcinogenesis inhibitor of the present invention include the high-risk groups having a high possibility of resulting in cancer such as smokers, persons having a high possibility of being suffered from cancer genetically or professionally, persons having a precancerous lesion such as colorectal polyp and persons once finishing the cancer therapy.

As to the applicable range of the carcinogenesis inhibitor of the present invention, there are exemplified various types of malignant and benign tumor such as melanoma, lymphoma, gastrointestinal cancer, lung cancer, esophageal cancer, stomach cancer, colorectal cancer (rectal cancer and colon cancer), ureter tumor, gallbladder cancer, bile duct cancer, breast cancer, liver cancer, pancreatic cancer, testicular tumor, maxillary (upper jaw) cancer, tongue cancer, lip cancer, oral cancer, throat cancer, ovary cancer, uterus cancer, prostate cancer, thyroid cancer, brain tumor, Kaposi's sarcoma, angioma, leukemia, polycythemia vera, neuroblastoma, retinoblastoma, myeloma, bladder tumor, sarcoma, osteosarcoma, cutaneous cancer, basal cell cancer, skin appendage cancer, cutaneous metastatic cancer and cutaneous melanoma. The carcinogenesis inhibitor of the present invention is particularly useful for the inhibition of colorectal cancer (rectal cancer and colon cancer). In addition, the carcinogenesis inhibitor of the present invention is useful in the prevention of not only for malignant tumor but also for benign tumor.

The carcinogenesis inhibitor of the present invention is useful not only for humans but also for other animals or, particularly, for any of mammals (such as mouse, rat, pig, fox, cat, rabbit, dog, cattle, horse, goat and monkey) being known to occur cancer and it is also able to be administered or ingested to those animals as a drug or a food.

The desirable dose of the present compound may vary depending upon the subject to be administered, dosage form, administering method, administering period, etc. and, in order to achieve the aimed effect, it is usual in the case of humans to orally administer to an adult in 1 to 10000 mg/day, preferably 50 to 5000 mg/day and, more preferably, 100 to 3000 mg/day in terms of the amount of the active ingredient. In the case of parenteral administration (such as an injection preparation), the effect can be expected usually in less dose than in the case of oral administration. Therefore, it is likely to be sufficient in a dose level of 3/1 to 1/10 of the above dose by oral administration.

EXAMPLES

The present invention will now be more specifically illustrated by way of the following Examples although the present invention shall be never limited thereto.

Test Example 1: Evaluation of Intestinal Polyp Formation (1) Grouping of Experimental Animals and Administration of a Test Substance As to an experimental animal, there was used a C57BL/6-Apc$^{Min/+}$ mouse (Min mouse) which was a familial adenomatosis coli model. The Min mouse is an Apc (adenomatous polyoisis coli) mutant mouse and an increase in polyp numbers is noted therein with time. It has been also known that the Min mouse is occurred with dyslipidemia in a state of highly oxidative stress. 5-week-old male Min mice were bred and acclimatized in a plastic cage (235×325×170 H mm) (six mice in maximum in a cage) in a laboratory where the temperature, the humidity and the brightness/darkness cycle were set at 24±2° C., 55% and 12 hours, respectively. In the meanwhile, they were freely ingested with filtered water and basic feed (MN-76A, CLEA Japan Inc.).

The experimental animals were randomly classified into a control group, a group to which 500 ppm of a test substance was administered and a group to which 1000 ppm of a test substance was administered. In each group, 10 mice per group were organized in such a manner that average body weight in the group became same. The control group was administered with a basic feed only and each of the 500 ppm test substance-administering group and the 1000 ppm test substance-administering group was administered with a mixed feed of a test substance (Compound 21) in 500 and 1000 ppm concentrations, respectively for eight weeks. No significant difference in the feed and in the body weight was noted among the groups during the administration period, and the daily ingested amount of the test substance in the group being administered with 500 ppm and 1000 ppm of the test substance was calculated to be 1.5 mg and 3 mg, respectively.

(2) Measurement of Numbers of Polyps in the Intestinal Tract

The mice in each group were killed under anesthetization at 13 weeks old and, after laparotomy, the intestinal tract was excised and fixed with formalin. Small intestine was divided into proximal segment (the segment in about 4 cm length from pylorus), middle segment and distal segment, then the polyp numbers in the four segments including colon were counted under a stereomicroscope and the mean value in each group was calculated. An example of the results is shown in Table 1.

In the meanwhile, the mucosa of the polyp part and the part where no polyp was formed (hereinafter, it will be referred to as "non-polyp part") in the proximal part of small intestine were excised and scraped upon anatomy and stored by freezing at −80° C. until being used in Test Examples 2 and 3.

TABLE 1

|  | Number of intestinal polyp | | | | |
|---|---|---|---|---|---|
|  | Small intestine | | | | |
|  | Proximal segment | Middle segment | Distal segment | Colon | Total |
| Control group (n = 9) | 5.78 | 11.67 | 29.33 | 0.67 | 47.44 |
| 500 ppm test substance-administering group (n = 9) | 3.89 | 7.33 | 27.00 | 1.00 | 39.22 |
| 1000 ppm test substance-administering group (n = 8) | 5.13 | 8.25 | 25.63 | 0.38 | 39.38 |

As shown in Table 1, total numbers of polyps decreased to an extent of about 17% in both of the groups being administered with 500 ppm and 1000 ppm test substances, and the polyp numbers in the middle segment of small intestine decreased to an extent of about 37% and 29% in each group as compared with the control group. As such, the present compound showed an excellent inhibitive action for the polyp formation.

Test Example 2: Evaluation of Cell Proliferation Ability in Polyp Part of Intestinal Mucosa The formalin-fixed slices embedded in paraffin prepared from the polyp part of mouse small intestine mucosa of the control group and of the 1000 ppm test substance-administering group being excised in Test Example 1 were dipped in xylene for five minutes×three times for the purpose of deparaffinization and were dipped in 99.5% alcohol for five minutes×three times to enhance the hydrophilicity followed by dipping into distilled water for 10 minutes. After that, the slices were dipped into a methanol solution containing 0.3% of hydrogen peroxide to conduct a deactivation treatment for the endogenous peroxidase. Further, 1 mL of a 0.3% Triton [Registered trade mark] X-100 solution containing 2% of horse serum (a phosphate-buffered saline (PBS) containing 0.3% of Triton) followed by blocking for 30 minutes.

To the slices was added an anti-mouse proliferating cell nuclear antigen (PCNA) antibody (Calbiochem [Registered trade mark]) diluted to an extent of 100 times and a primary antibody response was conducted overnight at 4° C. After washing with PBS for 5 minutes×three times, a labeled secondary antibody response was conducted using a biotinylated anti-mouse IgG antibody (H+L) (Vector Laboratories) as a secondary antibody and, after that, washing was conducted with PBS for 5 minutes×three times. Staining was conducted using a 3,3'-diaminobenzidine (DAB) solution and hydrogen peroxide. Incidentally, the counterstain (nuclear staining) was conducted using hematoxylin. After the nuclear staining, the response was ceased by washing with distilled water and, after treating with 100% ethanol for 5 minutes×three times, treatment with xylene was conducted for three times to seal. Positive responses of slides of the control group and of the 1000 ppm test substance-administering group were compared and observed under an optical microscope. The ratio of the PCNA antibody-positive cell numbers to the total cell numbers in the microscopic field in each group was also calculated. Examples of the results are shown in FIG. 1 and in Table 2.

TABLE 2

|  | Ratio of the PCNA antibody-positive cell numbers to the total cell numbers (%) |
|---|---|
| Control group (n = 20) | 71.26 |
| 1000 ppm test substance-administering group (n = 14) | 58.40 |

PCNA is a cell proliferation-associated protein expressed from the latter stage of a G1 phase (Gap1: preparatory phase for DNA synthesis) until the S phase (Synthesis: DNA synthesis phase) of the cell cycle, and is the so-called cell proliferation marker. It has been believed that, the higher the expression of the cell proliferation marker, the more the proliferation ability and the higher the malignancy level. When the PCNA antibody-positive cell numbers of polyp part of mouse small intestine mucosa excised from the mice of the control group and of the 1000 ppm test substance-administering group in Test Example 1 were measured, the result was that, as shown in FIG. 1 and Table 2, the PCNA antibody-positive cells stained in brown color (dark gray color in FIG. 1) decreased in the 1000 ppm test substance-administering group as compared with the control group. Incidentally, those in light purple color (light gray color in FIG. 1) are nuclear-stained cells. In view of the above, it has been noted that the present compound shows a proliferation inhibiting effect to the cells where the proliferation ability is promoted.

Test Example 3: Evaluation of Expression Level for Cell Proliferation-Associated Factor in Intestinal Mucosa and Polyp Part (1) mRNA Extraction from the Intestinal Polyp Part and Non-Polyp Part, and cDNA Synthesis TRIsol (Invitrogen) (500 µL) was added to a polyp part and a non-polyp part of small intestine mucosa of mouse of the control group and the 1000 ppm test substance-administering group scraped in Test Example 1. After 100 µL of chloroform was added thereto and mixed therewith, the mixture was centrifuged (12000 rpm for 2 minutes) and the supernatant liquid was recovered therefrom. The recovered supernatant liquid was added 250 µL of ethanol and RNA was extracted therefrom and purified using a column (QIAGEN).

After DNAse (Invitrogen) treatment, cDNA was prepared from 1 µg of the total RNA using High-Capacity cDNA Reverse Transcription Kits (Applied Biosystems).

Incidentally, the PCR reaction solution was prepared so as to make the total amount 20 µL using cDNA and SYBR Green Realtime PCR Master Mix (Toyobo).

(2) Evaluation of Expression Level of Proliferation-Associated Factors

Expression level of mRNA of the cell proliferation-associated factors [c-Myc, CDK4 and cyclin D1] was measured by a realtime-PCR method using the cDNA being synthesized from the total RNA extracted in the above (1). With regard to the polyp part, the mRNA expression level only of c-Myc was measured.

As to the PCR primers for each of the cell proliferation-associated factors, there were used c-Myc [Forward: GCCCGCGCCCAGACAGGATA (SEQ ID NO: 1), Reverse: GCGGCGGCGGAGAGGA (SEQ ID NO: 2)], CDK4 [Forward: ATGGCTGCCACTCGATATGAA (SEQ ID NO: 3), Reverse: TGCTCCTCCATTAGGAACTCTC (SEQ ID NO: 4)] and cyclin D1 [Forward: TGACTGCCGAGAAGTTGTGC (SEQ ID NO: 5), Reverse: CTCATCCGCCTCTGGCATT (SEQ ID NO: 6)]. Incidentally, MJ Research DNA Engine OPTICON 2 System (MJ Research) was used as to the realtime-PCR device. The PCR reaction was conducted in such a manner that, after heating at 94° C. for 15 minutes to linearize cDNA, steps of heat denaturation (at 94° C. for 20 seconds), annealing (at 60° C. for 30 seconds) and elongation reaction (at 72° C. for 30 seconds) were conducted for 39 cycles in total. Each of the resulted measured values was divided by the measured value of the glyceraldehyde-3-phosphate dehydrogenase (GAPDH) gene which was an internal standard whereupon the relative values were calculated. After that, the relative value of the 1000 ppm test substance-administering group was divided by the relative value of the control group whereupon the ratio of expression quantity of genes of the 1000 ppm test substance-administering group to the control group was calculated (n=3 in each group). Examples of the results are shown in Table 3 and Table 4.

TABLE 3

| | Ratio of expression quantity of cell proliferation-associated factor | |
|---|---|---|
| | Control group | 1000 ppm test substance-administering group (Non-polyp part) |
| c-Myc | 1.00 | 0.25 |
| CDK4 | 1.00 | 0.47 |
| Cyclin D1 | 1.00 | 0.27 |

TABLE 4

| | Ratio of expression quantity of cell proliferation-associated factor | |
|---|---|---|
| | Control group | 1000 ppm test substance-administering group (Polyp part) |
| c-Myc | 1.00 | 0.39 |

As shown in Table 3 and Table 4, the present compound inhibited the expression of the cell proliferation-associated factor in any of the polyp part and the non-polyp part in the small intestine of Min mice. In view of the above, it has been confirmed that the present compound inhibits the expression of the cell proliferation-associated factor and that, as a result, it inhibits the proliferation of the cell in the carcinogenic process.

Test Example 4: Evaluation of Safety of the Present Compound (1) Test Method

Eight healthy male adults (21 to 24 years age) (consisting of six cases being administered with the test substance and two cases being administered with the placebo) were used as the subjects and the present compound was orally administered repeatedly to evaluate the safety. A test substance (Compound 21) was orally administered in the single dose of 400 mg in such a manner that, on the first and the seventh day of the administration, once-daily in the morning on an empty stomach and, on the second to the sixth days of the administration, thrice-daily on an empty stomach (at 09:00, 14:00 and 19:00) together with 150 mL of water each (17 administrations in total).

(2) Results

In any of the cases, there was no clinical symptom suspected to be related to the present compound and there was also no abnormal variation suspected to be related to the present compound even in terms of blood pressure, pulse rate, body temperature, hematological test, blood biochemical test and urinary test.

INDUSTRIAL APPLICABILITY

In the pharmacological tests, the carcinogenesis inhibitor of the present invention showed an excellent inhibitive effect for the polyp formation and for the expression of cell proliferation-associated factor. Moreover, the carcinogenesis inhibitor of the present invention shows very high safety and achieves the effect by oral administration whereby its usefulness is very high as a chemoprevention agent being able to be utilized as pharmaceuticals, foods, etc. for humans and other animals having a risk of occurrence, recurrence and metastasis of cancer.

The invention claimed is:

1. A method for inhibiting a carcinogenesis, comprising administrating a inhibitor comprising, as an active ingredient, at least one member of a hydantoin derivative represented by the following formula (I) and a pharmaceutically acceptable salt thereof to a subject in need thereof:

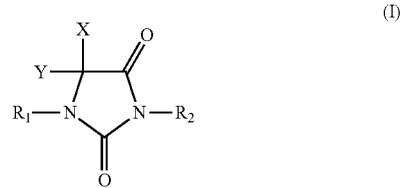

(I)

wherein $R_1$ is alkyl and $R_2$ is hydrogen and one of X and Y is hydroxyl and the other is hydrogen, hydroxy, alkyl or alkoxy.

2. The method according to claim 1, wherein one of X and Y is hydroxyl and the other is hydrogen, hydroxy or alkoxy having 1 to 3 carbon(s).

3. The method according to claim 1, wherein $R_1$ is alkyl having 1 to 3 carbon(s).

4. The method according to claim 1, wherein one of X and Y is hydroxyl and the other is hydrogen.

5. The method according to claim 1, wherein the carcinogenesis inhibition is done by a regulation of expression of cell proliferation-associated factors.

6. The method according to claim 5, wherein the carcinogenesis inhibition is done by an inhibition of expression of c-Myc, CDK4 or cyclin D1.

7. The method according to claim 1, wherein the inhibitor is a pharmaceutical composition.

8. The method according to claim 7, wherein the pharmaceutical composition is an oral preparation.

9. The method according to claim 1, wherein the inhibitor is a food composition.

10. The method according to claim 9, wherein the food composition is a health food or a supplement.

* * * * *

SEQUENCE LISTING

<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
gcccgcgccc agacaggata                    20

<210> SEQ ID NO 2
<211> LENGTH: 16
<212> TYPE: DNA
<213> ORGANISM: Artificial Sequence
<220> FEATURE:
<223> OTHER INFORMATION: Primer

<400> SEQUENCE: 2
gcggcggcgg agagga                        16

<210> SEQ ID NO 3
<211> LENGTH: 21
<212> TYPE: DNA
<213> ORGANISM: Artificial Sequence
<220> FEATURE:
<223> OTHER INFORMATION: Primer

<400> SEQUENCE: 3
atggctgcca ctcgatatga a                  21

<210> SEQ ID NO 4
<211> LENGTH: 22
<212> TYPE: DNA
<213> ORGANISM: Artificial Sequence
<220> FEATURE:
<223> OTHER INFORMATION: Primer

<400> SEQUENCE: 4
tgctcctcca ttaggaactc tc                 22

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
tgactgccga gaagttgtgc                    20

<210> SEQ ID NO 6
<211> LENGTH: 19
<212> TYPE: DNA
<213> ORGANISM: Artificial Sequence
<220> FEATURE:
<223> OTHER INFORMATION: Primer

<400> SEQUENCE: 6
ctcatccgcc tctggcatt                     19